US005601819A

United States Patent [19]
Wong et al.

[11] Patent Number: 5,601,819
[45] Date of Patent: Feb. 11, 1997

[54] BISPECIFIC ANTIBODIES FOR SELECTIVE IMMUNE REGULATION AND FOR SELECTIVE IMMUNE CELL BINDING

[75] Inventors: Johnson T. Wong, Westwood; Robert B. Colvin, Cambridge, both of Mass.

[73] Assignee: The General Hospital Corporation, Boston, Mass.

[21] Appl. No.: 305,856

[22] Filed: Sep. 14, 1994

Related U.S. Application Data

[63] Continuation of Ser. No. 75,343, Jun. 10, 1993, abandoned, which is a continuation of Ser. No. 683,254, Apr. 10, 1991, abandoned, which is a continuation-in-part of Ser. No. 231,193, Aug. 11, 1988, abandoned.

[51] Int. Cl.$^6$ .......................... G01N 33/53; C07K 16/00; A61K 39/395
[52] U.S. Cl. .......................... 424/136.1; 435/5; 435/7.2; 435/7.24; 530/387.3; 530/388.1; 530/388.2; 530/388.22
[58] Field of Search .......................... 424/136.1; 435/7.1, 435/5, 7.24, 7.2; 530/350, 387.1, 388.1, 388.2, 388.22, 387.3; 935/15

[56] References Cited

U.S. PATENT DOCUMENTS

| | | | |
|---|---|---|---|
| 4,361,549 | 11/1982 | Kung et al. | 424/85 |
| 4,361,550 | 11/1982 | Kung et al. | 426/85 |
| 4,363,799 | 12/1982 | Kung et al. | 424/85 |
| 4,364,932 | 12/1982 | Kung et al. | 424/85 |
| 4,364,933 | 12/1982 | Kung et al. | 424/85 |
| 4,364,934 | 12/1982 | Kung et al. | 424/85 |
| 4,364,935 | 12/1982 | Kung et al. | 424/85 |
| 4,364,936 | 12/1982 | Kung et al. | 424/85 |
| 4,364,937 | 12/1982 | Kung et al. | 424/85 |
| 4,381,295 | 4/1983 | Kung et al. | 424/85 |
| 4,542,225 | 9/1985 | Blattler et al. | 548/473 |
| 4,925,648 | 5/1990 | Hansen et al. | 424/1.1 |

FOREIGN PATENT DOCUMENTS

| | | |
|---|---|---|
| 63763 | 6/1982 | European Pat. Off. . |
| 96076 | 12/1982 | European Pat. Off. . |

OTHER PUBLICATIONS

Allison et al., "Structure, Function, and Serology of the T–Cell Antigen Receptor Complex," Ann. Rev. Immunol. 5:503–40 (1987).
Anderson et al., "Cross–Linking of T3 (CD3) with T4 (CD4) Enhances the Proliferation of Resting T Lymphocytes," The Journal of Immunol. 139:678–682 (1987).
Bank et al., "Perturbation of the T4 Molecule Transmits a Negative Signal to T Cells," J. Exp. Med. 162:1294–1303 (1985).
Bernard et al., "A Novel Human Leukocyte Differentiation Antigen," The Journal of Immunol. 132:2338–2344 (1984).
Emmrich et al., "Synergism in the Activaton of Human CD8 T Cells by Cross–Linking the T–Cell Receptor Complex with the CD8 Differentiation Antigen," Proc. Natl. Acad. Sci. USA 83:8298–8302 (1986).

Fleischer et al., "Function of the CD4 and CD8 Molecules on Human Cytotoxic T Lymphocytes: Regulation of T Cell Triggering," The Journal of Immunol. 136:1625–1628 (1986).
Kaye et al., "The Fab Fragment of a Directly Activating Monoclonal Antibody . . . " J. Exp. Med. 159:1397–1412 (1984).
Kipps et al., "Importance of Immunoglobulin Isotype in Human Antibody–Dependent, Cell–Mediated Cytotoxicity Directed by Murine Monoclonal Antibodies," The Journal of Exp. Med. 161:1–17 (1985).
Landau et al., "The Envelope Glycoprotein of the Human Immunodeficiency Virus Binds to the Immunoglobulin–Like Domain of CD4," Nature 334:159–162 (1988).
Lazarovits et al., "Lymphocyte Activation Antigens," J. Immunol. 133:1857–1862 (1984).
Leontsini et al., "Physical and Functional Association of the T Cell Receptor and the T3 Molecular Complex on Cytotoxic T Cells Clones . . . " Cellular Immunology 102:21–32 (1986).
Mason et al., "Effector Mechanisms in Allograft Rejection," Ann. Rev. Immunol. 4:119–45 (1986).
McMichael et al., *Leucocyte Typing III*, Springer–Verlag, Heidelberg (1987).
Milstein et al., "Hybrid Hybridomas and Their Use in Immunohistochemistry," Nature 35:537–40 (1983).
Moretta et al., "Clonal Heterogeneity in the Requirement for T3, T4, and T8 Molecules in Human Cytolytic T Lymphocyte Function," J. Exp. Med. 159:921–934 (1984).
Morimoto et al., "The Isolation and Characterization of the Human Suppressor Inducer T Cell Subset," J. of Immunol. 134:1508–15 (1985).
Morimoto et al., "The Isolation and Characterization of the Human Helper Inducer T Cell Subset," J. of Immunol. 134:3762–69 (1985).
Parham, Peter, "In Vitro Production of a Hybrid Monoclonal Antibody that Preferentially Binds to Cells that Express Both HLA–A2 and HLA–B", Human Immunology 12:213–21 (1985).
Perez et al., "Specific Targeting of Human Peripheral Blood T Cells by Heteroaggregates Containing Anti–T3 Crosslinked to Anti–Target Cell Antibodies," J. of Exp. Med. 163:166–17 (1986).
Reinherz et al., "Subpopulations of the T4+ Inducer T Cell Subset in Man," J. of Immunol. 126:67–70 (1981).
Sattentau et al., "Epitopes of the CD4 Antigen and HIV Infection," Science 234:1120–23 (1986).
Shaw et al., "Susceptibility of Cytotoxic T Lymphocyte (CTL) Clones to Inhibiton by Anti–T3 and Anti–T4 . . . " J. of Immunol. 134:3019–26 (1985).

(List continued on next page.)

*Primary Examiner*—Toni R. Scheiner
*Attorney, Agent, or Firm*—Fish & Richardson, P.C.

[57] ABSTRACT

Bispecific antibodies can be used to alter the ratio and proliferation of T cell subsets, to selectively target cells that coexpress two different surface antigens such as the activated T cell subsets, or to block the cytolytic function of specific T cell subsets.

34 Claims, 4 Drawing Sheets

OTHER PUBLICATIONS

Staerz, "Hybrid Hybridoma Producing a Bispecific Monoclonal Antibody that Can Focus Effector T-Cell Activity," Proc. Natl. Acad. Sci., 83:1453–57 (1986).

Terasaki et al., "Microdroplet Testing for HLA-A, -B, -C and -D Antigens," A.J.C.P. 69:103–20 (1978).

Van Wauwe et la., "OKT3: A Monoclonal Anti-Human T Lymphocyte Antibody with Potent Mitogenic Properties," J. of Immunol. 124:2708–13 (1980).

Walker et al., "Activation of T Cells by Cross-Linking an Anti-CD3 Antibody with a Second Anti-T Cell Antibody: Mechanism and Subset-Specific Activation," Eur. J. Immunol. 17:873–80 (1987).

Wong et al., "The Journal of Allergy and Clinical Immunology", vol. 77, No. 1, Part 2, p. 229, Abstract 434, Jan. 1986.

Wong et al., "Bi-Specific Monoclonal Antibodies: Selective Binding and Complement Fixation to Cells that Express Two Different Surface Antigens," J. of Immunol. 139:1369–74 (1987).

Wong et al., The FASEB Journal, vol. 2, No. 6, Abstract 8898, Mar. 25, 1988.

MONOSPECIFIC MONOCLONAL ANTIBODIES

BISPECIFIC MONOCLONAL ANTIBODIES

BISPECIFIC ANTIBODIES FOR SELECTIVE IMMUNE REGULATION AND FOR SELECTIVE IMMUNE CELL BINDING

This invention was made, at least in part, using funds supplied by a grant from the United States Government, and the Government has rights in the invention.

This is a continuation of application Ser. No. 08/075,343, filed Jun. 10, 1993, now abandoned, which is a continuation of application Ser. No. 07/683,254 filed on Apr. 10, 1991 now abandoned, which is a continuation-in-part of application Ser. No. 07/231,193 filed on Aug. 11, 1988 now abandoned.

BACKGROUND OF THE INVENTION

This invention relates generally to the field of antibodies that specifically bind to surface antigens of human cells, particularly human T lymphocytes or "T cells"; it also relates to methods for using those antibodies.

The antigen-specific immune system comprises a variety of differentiated T cells (thymus-derived lymphocytes) and B cells (bone-marrow-derived lymphocytes). Different categories and sub-categories of lymphocytes are defined by expression of different cell-surface antigens. Specifically, various categories and sub-categories of T cells have been identified by characteristic patterns of cell-surface antigen expression. While some functional correlations with these antigens have emerged, many aspects of T-cell function remain to be elucidated.

McMichael and Gotch provide a review of T-cell antigens and antibodies supplied by a large number of workers in the field. They categorize the antibodies by so-called cluster designations ("CD's") of the IUIS-WHO nomenclature committee. See, McMichael and Gotch, "T-cell antigens: New and previously defined clusters" Ch. 5.1 in *Leucocyte typing III*, Springer-Verlag, Heidelberg (1987). See also, Bernard et al., *Leucocyte typing*, Springer-Verlag, Heidelberg (1984); and Reinhertz et al., *Leucocyte typing II*. Springer-Verlag, Heidelberg (1986). Among the widely accepted categories of T cells are: so-called CD4+(or T4) cells, which comprise the majority of the helper-inducer cells and are a specific target of the AIDS virus; and CD8+(or T8) cells, which comprise the majority of the cytotoxic and suppressor cells. T4 cells bear the CD3 antigen which is generally characteristic of all T cells and the CD4 antigen which is specific among T cells to T4 cells. T8 cells bear CD3 and CD8 antigens.

Various monoclonal antibodies which differentiate T-cell subpopulations are known (Ortho Pharmaceuticals, Raritan, N.J.) U.S. Pat. Nos. 4,361,549 (OKT3 ATCC CRL 8001); 4,361,550 (OKT8, CRRL 8014); 4,363,799 (OKT1); 4,364,932 (OKT5); 4,364,933 (OKT6); 4,364,934 (OKT9); 4,364,935 (OKT10); 4,364,936 (OKM1); 4,364,937 (OKT11); and 4,381,295 (OKT4, ATCC CRL 8002).

CD3, in combination with Ti, the antigen binding structure, forms the T cell receptor complex (TCR). The major function of TCR appears to be in signal transduction (reviewed by Allison and Lanier, *Ann. Rev. Immunol.* 5:503–540 (1987)). The effects on T cell function, when antibody binds to the CD3 antigen, are complex.

Van Wauwve et al., *J. Immunol.* 1124:2708–2713 (1980) reported that OKT3 monoclonal antibody (MAB), when provided in solution containing peripheral blood mononuclear cells, induces mitogenesis of the T lymphocytes. Monoclonal antibodies are generally bivalent, i.e., they have two FAB sites that specifically recognize the same target. Thus, it has been proposed that T cell proliferation is initiated by cross-linking of two CD3 antigens by the bivalent anti-CD3 monoclonal antibody (OKT3). See, e.g., Allison and Lanier, *Ann. Rev. Immunol.* 5:503–540 (1987). Van Wauwe and others who have presented monovalent anti-TCR antibody report weak or ineffective proliferation. (Kaye et al. *J. Exp. Med.* 159:1397–1412 (1984)).

Others have studied the effect of anti-CD4 or anti-CD8 antibody on anti-CD3-induced-T-cell proliferation. In one case, the effect was reported to be inhibitory, and in another case it was reported to augment proliferation. Bank and Chest, *J. Exp. Med.* 162:1294 reported that binding of the CD4 by MAB in a soluble state sends a strong inhibitory signal. Fleischer et al., *J. Immunol.* 136:1625 showed that soluble CD8 binding also sends an inhibitory signal. In contrast, Anderson et al., *J. Immunol.* 139:678–682 disclosed that when the anti-CD4 or anti-CD8 MAB is absorbed to the same bead surface as an anti-CD3 MAB, there is a strong augmentation to proliferation. Emmrich et al., *Proc. Nat'l. Acad. Sci. USA* 83:829808301 (1986) also reported that anti-CD8 MAB and anti-CD3 MAB, when attached to the same plastic surface, significantly enhanced proliferation of CD8 cells.

Still others have studied the effect of linking antibodies which are exclusively expressed on different cell types. For example, Perez et al., *J. Exp. Med.* 163:166–178 (1986) report that T cells, sensitized with anti-CD3-antibody which has been covalently linked to antibodies to tumor cell targets, will lyse the tumor targets. Stearz and Bevan, *Proc. Nat'l. Acad. USA* 83:1453–1457 (1986) disclose a mouse hybrid hybridoma cell line produced from parental hybridomas whose antibodies recognize, respectively, murine T-cell receptor complex (F23.1, a murine IgG2a) and a murine Thy-1.1 alloantigenic determinant. The bispecific monoclonal antibodies produced by the hybrid hybridoma induced lysis of cells bearing the Thy-1.1 target antigen.

The binding regions of bispecific monclonal antibodies have been further modified in an attempt to increase binding to target cells and thereby further stimulate the release of cytokines. *Immunol. Today* 12:51 (1991).

Moretta et al., *J. Exp. Med.* 159:921 (1984) reported the relative effectiveness of anti-CD3, anti-CD4, and anti-CD8 MABs in blocking cytolytic functions and found considerable clonal heterogeneity. These experiments were done in the continuous presence of the MABs.

SUMMARY OF THE INVENTION

As detailed below, bispecific antibodies, particularly bispecific monoclonal antibodies, can be used to selectively destroy and proliferate different T cell subsets, to selectively target cells that coexpress two different surface antigens such as the activated T cell subsets, or to block the cytolytic function of specific T cell subsets. Trispecific antibodies may be formed by incorporting a third binding site in the $F_c$ portion of the antibody, and may further promote lysis or may selectively deliver a drug, toxin or stain.

I. Selective Destruction and Proliferation of T Cell Subsets

We have discovered that bispecific antibodies which exhibit specificity both to the human CD3 antigen and to a second human T-cell surface antigen, can be administered to a mixture of different types of T cells, causing selective proliferation and destruction of the T cell subsets. Accordingly, one aspect of the invention generally features a method for decreasing the ratio of human TY cells/human TZ cells in a mixture of cells, where TY cells and TZ cells are symbols we use as general designations of different T cell subpopulations, each of which bears the CD3 antigen. TY cells also bear a second human T cell surface antigen not present on TZ cells. The method comprises contacting a mixture of cells with the above described bispecific antibody, which we designate generally as CD3, Y.

In preferred embodiments of this aspect of the invention, the bispecific antibody is a bispecific monoclonal antibody or "BSMAB" (for example, an antibody formed by a hybrid hybridoma or other clonal cell); the resulting monoclonal antibody has a common Fc portion and one FAB portion from each parental hybridoma. Thus, one FAB portion is CD3-specific and the other is specific for the second target antigen (TY-specific). While bispecific monoclonal antibodies are preferred, other types of bispecific antibodies can be used in the invention. For example, the technique of Paulus EP 096076 can be used in which the FAB portions from two different antibodies are separated and then joined covalently. Alternatively, the covalent linkage method of Perez et al. (cited above) can be used.

Also in preferred embodiments, the cells remaining after contact with the bispecific antibody are cultured to amplify the cells that have not been destroyed. The net result is the destruction of TY cells and the proliferation of TZ cells.

The method is useful for disease conditions or circumstances in which selective boosting or suppression of the immune system is desired. For example, patients infected with HIV virus are at risk for a fatal decrease in T4 cells. The method can be used to selectively proliferate T4 cells of such patients by contacting a mixture of the patient's peripheral blood cells with the antibody. At the same time the method reduces the relative numbers of T8 cells which can suppress the immune response and thereby can be detrimental to immunocompromised patients.

Conversely, for patients having an undesired immune activity, such as those experiencing an auto-immune disease (e.g. lupus and type I Diabetes mellitus) or patients undergoing graft rejection, it may be desirable to reduce the level of T4 cells and to proliferate T8 cells. In that case, a CD3,4 bispecific antibody could be used.

The method can be directed to very specific subtypes of T cells. For example, T4 cells can be divided into subgroups: T4 inducer/helper cells and T4 inducer/suppressor cells. Morimoto et al., *J. Immunol.* 134:1508 (1985); Morimoto et al., *J. Immunol.* 134:3762 (1985); Reinherz et al., *J. Immunol.* 126:67 (1981); and Morimoto et al., *J. Clin. Invest.* 128:1645 (1982). For patients undergoing an undesired immune activity, such as graft rejection or auto-immune disease, T4 inducer/helper cells can be selectively depleted while maintaining the T4 inducer/suppressor function. In that case, a bispecific CD3, w29 antibody can be used, e.g. using a hybridoma that is a hybrid of a CD3-specific hybridoma and the Leu8 hybridoma (Becton Dickinson) or the K20 hybridoma of Bernard et al., *J. Immunol.* 132:3228 (1984). If desired, a CD3,8 BSMAB may be concurrently or sequentially added in vitro to eliminate the T8 cells and allow the proliferation of the purified T4 inducer/suppressor.

In the converse situation, where it is desirable to maintain the inducer/helper function and to eliminate or reduce the inducer/suppressor function, a CD3, CD45R bispecific antibody can be used, e.g., using a hybridoma that is a hybrid of a CD-3-specific hybridoma and the 4B4 hybridoma of Morimoto et al., *J. Immunol.* 134:1508 (1985).

In a parallel fashion, CD8 bearing cells can be divided into cytotoxic and suppressor T8 cells. In order to control graft rejection or other undesired immune responses, the invention can be used to selectively destroy cytotoxic T8 cells, using a bispecific antibody for CD3 and CD28, e.g. using a hybridoma that is a hybrid of a CD3-specific hybridoma and the 9-3 or UCHTI. See McMichael and Gotch cited above. In that way, the suppressor T8 cells are left intact.

II. Selective Targeting of Cells that Coexpress Two Different Surface Antigens

A limitation of selective immunotherapy using conventional MABs is that not all desired target cell populations can be characterized by a single unique surface antigen. Many surface antigens are also expressed in cells other than the desired target. For example, activated lymphocytes of the T4 subset may be characterized by the combination of an activation marker such as the IL2 receptor and CD4 antigen; but either antigen alone may be found in other cell populations.

Accordingly, a second aspect of the invention features a method of selectively killing target cells which bear at least two different surface antigens, Y and Z, where the target cells are a part of a mixture of cells (in vivo or in vitro), at least some of which bear Y without Z or Z without Y. The mixture of cells is contacted with a BSMAB having a common Fc portion, one FAB portion specific for Y and one FAB portion specific for Z. The BSMAB specifically binds the target cells. To kill the bound cells, the patient's own immune system can be recruited. For example, the antibody-dependent cell-mediated cytotoxicity (ADCC) system will destroy antibody bound cells. The antibody-dependent complement-mediated cytotoxicity (ADCMC) system will also kill those cells when appropriate complement is present. In preferred embodiments of this method, the target cells are T cells, or subpopulations of T cells.

A third aspect of the invention features the use of BSMAB to specifically bind a target T-cell subpopulation by contacting a mixture of T cells with a bispecific monoclonal antibody CDY, Z, where CDY represents a T cell surface antigen and Z represents a different surface antigen, permissibly, not necessarily, one specific for T cells or T-cell subpopulations. The target population is substantially the only population of cells in the mixture which expresses both the CDY and the Z antigen. This method can be used to detectably label the target subpopulation by linking a detectable label to the BSMAB. Similarly, the method can be used to deliver a drug or toxin to the target population by linking a drug or toxin to the BSMAB. Finally, the method can be used to kill the target population by exposing the BSMAB-bound cells to an effector system, such as ADCC or ADCMC. Preferably the BSMAB is selective for cells which are CD4-bearing T cells, CD8-bearing T cells, CD4 inducer/helper cells, CD4 inducer/suppressor cells, CD8 cytotoxic cells, or CD8 suppressor cells. The method can also be used with BSMABs which have a common Fc portion, a first FAB portion specific for CD3, CD4, or CD8, and a second FAB portion specific for a cell activation marker, such as the transferrin receptor or the interleukin-2 receptor.

In both the second and third aspects of the invention, the target cells are the only cells in the mixture that express both of the antigens. The bispecific monoclonal antibodies exhibit a particularly high avidity for the target population and assist in identifying targets which otherwise cannot be specifically selected because non-target cells may also express one of the antigens. For example, activated lymphocytes of the T4 subset may be characterized by the combination of an activation marker such as the interleukin 2 (IL2) receptor and the CD4 antigen, but not by either antigen alone. The higher avidity exhibited probably reflects the difficulty in simultaneously breaking both bonds between the BSMAB and the target cells, whereas it is necessary only to break a single bond when only one of the antigens is present on the cell surface as for non-target cells. This selective avidity toward cells that coexpress two different surface antigens is not limited to BSMABs that have CD3 binding activities.

III. Inhibition of Cytolytic T Cell Function cytolytic T cells have been shown to be important mediators of graft rejection as reviewed by Mason and Morris, *Ann. Rev. Immunol.* 4:119–145 (1986). A fourth aspect of the invention features CD3,8 and CD3,4 BSMABs (applied in a different protocol than used for selective destruction and proliferation) to selectively inhibit the cytolytic function of T8 and T4 cytolytic cells in a more effective way than anti-CD3 or anti-CD8 MABs. Both the CD3 antigen and the CD8 antigen of T8 cytolytic cells are involved in the cytolytic process.

IV. Novel BSMABs

A fifth aspect of the invention features a number of bispecific monoclonal antibodies that are useful in the above described methods. In particular, for various applications for CD4-binding antibodies, antibodies recognizing the OKT4 epitope do not provide optimal results. Accordingly, we prefer to use anti-CD4 antibodies recognizing other epitopes, such as OKT4a, Leu3a, EDU-2, T4/19Thy 5D7, F101-65, 94bi, 91D6, or MT310. See Sattentau et al., *Science* 234:1120 (1986) and Landau et al., *Nature* 334:159–162 (1988). In particular, we have developed an anti-CD4 hybridoma (JET 4b) which is substantially non-competitive with OKT4, meaning that its antibody will impart a detectable stain in the presence of at least 100-fold excess OKT4 antibody. Similarly, we have produced anti-CD8 BSMABs that substantially do not compete with OKT8.

Other useful bispecific antibodies specifically target activated cells in a T-cell subpopulation, e.g. activated CDY cells (where Y=3, 4, or 8). These antibodies have a common Fc portion and an FAB portion specific for CDY. The other FAB portion is specific for a cell activation marker (e.g. the IL2 receptor) or the transferrin receptor (14B5, recognized by OKT9).

V. Trispecific Monoclonal Antibodies TSMABs

A sixth aspect of the invention features the modification of the $F_c$ region of the BSMAB to provide an addtional binding site. The $F_c$ region may be modified to include this third binding site, or the $F_c$ region may be entirely replaced by the third binding site. In particular, the additional binding site may be anti-CD3 or anti-Ti.

Other useful modifications of the $F_c$ region would provide binding sites for desired drugs or toxins. Alternatively, the $F_c$ region would bind a staining enzyme.

DESCRIPTION OF THE PREFERRED EMBODIMENT

SELECTIVE PROLIFERATION AND DESTRUCTION OF T-CELL SUBPOPULATIONS

The following examples illustrate the invention using specific CD3,4 or CD 3,8 bispecific monoclonal antibodies. However, the invention is not limited to this combination of antigen specificity or to hybrids produced from the parent hybridomas disclosed. Those skilled in the field will determine readily that the following examples are merely illustrative of the general technique of selective T cell destruction and proliferation.

In general, bispecific antibodies (particularly BSMABs) that are useful in the method of selective proliferation and destruction of T-cell subpopulations have CD3 antigen specificity as one of their two binding specificities. The other binding specificity is preferably CD4 or CD8, but it can be any sub-population of T4 cells or T8 cells, or any of the other categories of T cells, such as those recognized by the IUIS-WHO nomenclature committee.

While we do not wish to be bound to a theory, it appears that the CD3, Y bispecific antibody can bind one FAB portion to the CD3 antigen on either subpopulation of T cells, and concurrently the second FAB portion can bind to a surface molecule on either the same cell or a nearby cell, or the second FAB portion can remain unbound. We have found that, similar to direct crosslinking of two CD3s on the same cell, these events have the potential to activate and proliferate the T cell, as described later. It is believed that the bispecific antibody does bridge between TY, the T-cell subpopulation to be decreased, and any other CD3-bearing cell. This can occur, even though the CDY molecule and CD3 complex are both expressed on the TY cells. Probably, when cells randomly come together the CD3, Y bispecific monoclonal antibodies bridge the two cells, causing the cells to adhere to each other and allowing more CD3, Y antibodies to bridge the two cells. For CD3 bearing cells having cytolytic capability, this bridging will then cause the destruction of the TY cell, and this destruction is a sufficiently rapid and frequent event to enable this method to effectively alter the ratio of TY to TZ cells. This effect may also reflect selective destruction of the TY cells by antibody-dependent cell-mediated cytotoxicity (ADCC) by Fc receptor bearing cells that also are frequently present in the body fluid or tissues. The net effect is a decrease of the TY population as the TZ population is increased.

A. Making the Hybrid Hybridomas and Obtaining Bispecific Monoclonal Antibodies The hybrid hybridomas used in the invention are formed by fusing two hybridomas according to the general polyethylene glycol fusion protocol of Preffer et al., *J. Immuno.* 133:1857 (1984). See also, Reading EP 068763; Stearz and Bevan, *Proc. Nat'l. Acad. Sci. USA* 83:1453–1457 (1986); and Milstein et al., *Nature* 305:537–540 (1983). More specifically, one fusion partner is a hypoxanthine-guanine phosphoribosyltransferase (HGPRT)-deficient clone of one parental hybridoma (e.g., a CD4-binding monoclonal antibody producer, such as OKT4 (Ortho Diagnostics, Raritan, N.J.), Leu3a (Becton Dickinson), or JET 4a, 4b, or 4c (described below)). Similarly, HGPRT-deficient clones of CD8-binding monoclonal antibody producers, such as OKT8 or 3G3, are used. HGPRT-deficient clones are obtained by growing the clones in increasing concentrations of 8-azaguanine (GIBCo, Grand Island, N.Y.; 1 µg/ml to 20 µg/ml).

The other fusion partner is thymidine kinase (TK)-deficient, which is selectively grown in the presence of increasing concentrations of 5-bromodeoxyuridine (Sigma Chemical Co., St. Louis, Mo.; 3 µg/ml to 60 µg/ml). Examples include CD3 binding monoclonal antibodies such as 12F6, or antibodies that bind to activation markers such as the interleukin 2 receptor or transferrin receptor.

The HGPRT deficient clone from one parental hybidoma is fused to TK deficient clone of the other parental hybridoma with PEG. After fusion, the desired hybrid hybridomas are selected in hypoxanthine-aminopterin-hymidine (HAT) supplemented media. The media consists of Isocove's modified Dulbecco's medium with 10% fetal calf serum, 2mM glutamine, and 5 ug/ml gentamicin. Cells deficient in HGPRT and in TK complement each other and only the fused cells grow in the presence of HAT. Alternatively, the HAT-sensitive parenteral hybridomas may be additionally rendered neomycin-resistant by transfecting them with an incomplete retroviral vector containing the neomycin resistant gene. To produce the desired BSMAB, one of these doubly selected parental hybridomas will be fused to the appropriate unselected (naturally HAT-resistant neomycin-sensitive) other parental hybridoma. Only the fused hybrid-hybridomas will survive in the selection medium containing G418 (GIBCO), a neomycin analogue, and HAT. A third method that we have is based on a modification of the chemical hybridization method of Nisonoff and Palmer to obtain rapidly new BSMABs from the parental antibodies (27). 100 mM 2-mercaptoethanolamine was added to a mixture of the parental mAbs to reduce their inter-chain disulfide bonds. The reduced parental mAbs were then split into two half Ig molecules by disrupting the noncovalent inter-heavy chain bonds with buffers containing 25 mM NaCl at pH 2.5. The half Ig molecules were then allowed to reanneal randomly by dialyzing into a neutral PBS solution at pH 7.4.

Screening is accomplished by standard indirect staining method consisting of incubation of peripheral blood or other antigen expressing cells with the culture supernatants at 4° C., followed by incubation with fluorescein isothiocyanate (FITC)-conjugated goat anti-mouse IgG antibodies (TAGO, Inc., Burlingame, Calif.). The result may be checked by flow cytometry. See Wong and Colvin, *J. Immunol.* 139:1369–1374 (1986).

The bispecific monoclonal antibody can be obtained either from the supernatant of the hybrid hybridoma or from the ascites fluid of mice injected with the hybrid hybridoma, and purified by isoelectric focusing. Other purification techniques such as affinity chromatography using sequential mouse anti-idiotype anti-isotype monoclonal antibodies or high performance liquid chromatography may be used.

B. Selective Proliferation and Destruction

There is a delicate balance between inadequate protection against foreign invasion on the one hand and wasted resources or autoimmune disease on the other. This balance is reflected in the balance of various types of effector and suppressor systems within the immune system.

Various disease states manifest a serious change in the normal balance of different T-cell populations. Some involve compromised ability to mount an immune response, e.g. a deficiency in the CD4 T-cell population caused by T4-specific viral infection such as AIDS. Others involve an undesirable immune response such as lupus, rheumatoid arthritis, Type I diabetes mellitus other autoimmune diseases, or rejection of an allograft.

We have discovered that, notwithstanding the various competing phenomena which may be predicted from existing theories, the predominant effects of administration of the CD3, Y bispecific antibodies according to the invention are to specifically destroy T cells bearing the Y antigen and to concurrently proliferate the residual CD3 bearing cells. For example the addition of CD3,4 BSMAB to a mixed population of peripheral blood mononuclear cells or from culture will lead to marked depletion of T4 cells and proliferation of the T8 cells in a dose-dependent fashion. The addition of CD3,8 BSMAB to similar mixed population will lead to depletion of the T8 population with proliferation of the T4 population.

The techniques for applying CD3,4 and CD3,8 BSMABs in vitro are described below.

Fresh peripheral blood was collected in heparinized tube from subjects. Peripheral blood mononuclear cells (PBMC) were obtained by Ficoll-Hypaque (Pharmacia) centrifugation. PBMC were set up at a concentration of $10^6$ cells/ml except where noted. The media were RPMI+10% fetal calf serum (FCS) or 5% normal human serum+50 µg/ml gentamycin (all from GIBCo., Grand Island, N.Y.)+10–20U rIL2/ml [Cetus Corp., Emeryville, Calif.)] except where noted. CD3,4 or CD3,8 bispecific antibodies were then added at the concentration of 3–5 ug/ml (one may use a range of 0.5–30ug/ml, though with lower concentration one observes progressively less depletion of the T4 and T8, respectively, but the degree of cellular proliferation is retained). The culture were incubated at 37° C., 5%$CO_2$ for 2–4 days, and then the media were partially exchanged for fresh media without the MAB. The cultures were then expanded to keep the cells between 0.2–2×$10^6$ cells/ml. The purity of the desired cells may then be checked from day 5 onward by staining with the appropriate fluorochrome-conjugated MABs (including anti-CD3, anti-CD4, and anti-CD8 MABs) and performed on a flow cytometer. Proliferation is determined by cell count. In nearly all subjects tested where fresh peripheral blood mononuclear cells were used, the CD3,4 BSMAB had caused a marked reduction of the percentage of the CD4+ cells for all subjects. The level of surface CD4 antigen expression on any residual CD4+ cells was usually very low as judged by flow cytometry. CD3,4 led to a marked proliferation of the CD8+ T cells resulting in an increase in the percentage and absolute number. The CD3,8 BSMAB yielded similar results with the reciprocal T-cell subsets and effected a marked reduction in the percentage of CD8+ population in all subjects. Any residual CD8+ cells also generally expressed only a low level of CD8 surface antigen as judged by flow cytometric staining. The CD4+ population increased in percentage and in absolute number in the presence of CD3,8 BSMAB. The parental anti-CD3 MAB 12F6 (CD3,3) induced proliferation of both populations but in most cases there was a greater net expansion of the CD8+ population than the CD4+ population.

There was a progressive increase in both purity and degree of expansion of the CD8+ T cells and decrease in CD4+ T cells with increasing CD3,4 BSMAB concentrations until an optimum was reached at concentrations between 3–5 µg/ml. The optimum concentrations in regard to the enrichment of the CD4+ percentage, the CD4+ proliferation, and the decrease of CD8+ percentage occurred at the range of 3–5 µg/ml of the CD3,8 BSMAB. Above these concentrations both the CD4+ percentage and proliferation deteriorated. For CD3,4 the best enrichment of the CD8+ percentage and reduction of the CD4+ percentage occurred at the concentration range 1–2×10$^6$ cells/ml. For CD3,8 BSMAB-mediated enrichment of the CD4+ population and depletion of the CD8+ population, the optimum results occurred at the concentration range of 0.5–1.0×10$^6$ cells/ml. Above the optimum concentration there was a progressive decrease in the CD4+ percentage and increase in the CD8+ percentage.

There was a progressive enrichment of the CD8+ population and depletion of the CD4+ population with increasing duration of antibody treatment from 0.25 hrs. to 48 hrs., with most of the selectivity seen within the first 24 hrs.

Both T cell proliferation and cytotoxicity require or are enhanced by IL2, which may be endogenous or exogenous. There is a nearly linear increase of both enrichment and proliferation of the desired T cell subset with the log of the exogenous IL2 added up to 20 U/ml. There were no further increases in the concentration range 20–100 U/ml.

This method can also be used to obtain CD4+ and CD8+ T cell clones directly from both mixed normal cells or HIV-infected cells when the above procedure was performed under limiting dilution condition.

The ability of the CD3,4 and CD3,8 BSMAB to selectively lyse the T4 and T8 cells respectively via bridging of the CD4 or CD8 of the target cell to the CD3 of the effector cells can be demonstrated with a chromium release assay. By mixing purified chromium labelled T4 or T8 cells with unlabelled purified effector cells and observing chromium release as evidence of cytolysis, we observed that the major effector of T4 lysis in the presence of CD3,4 BSMAB are the T8 cells. In contrast, both the T4 and T8 can mediate lysis of the T8 population in the presence of the CD3,8 BSMAB.

Even though these BSMABs cannot directly link two CD3s together, we can nevertheless demonstrate excellent proliferation of both the T4 and T8 cells induced by either the CD3,4 or CD3,8 BSMAB at the 3–5 ug/ml concentration used. These studies were performed by measuring tritium-labelled thymidine incorporation as evidence of DNA synthesis. At lower concentrations and in the absence of adherent cells, CD3,8 induces a much stronger proliferative signal in the T8 cells than in the T4 cells. CD3,4 induced a slightly stronger proliferative signal in the T4 cells than in the T8 cells under similar conditions.

For lymphocytes from blood or other body fluids, the CD3,4 and CD3,8 BSMABs offer several distinct advantages over existing selection systems. In contrast to the high cell losses in flow cytometry and panning, and the moderate cell loss associated with antibody/complement (due to repeated washings and DNA-induced cell adhesions), the CD3,4 and CD3,8 BSMABS yield little loss and in fact induce excellent proliferation of the desired subpopulation without the necessity of adding another stimulatory agent. The procedure involves simple addition of the antibody and does not require repeated manipulations such as incubation washing, or staining. This is less likely to cause contamination of the culture and in particular of the laboratory personnel. It also saves considerable time. Unlike flow cytometry, expensive instruments and well-trained personnel are not needed. These advantages are important where the desired subpopulation is a small fraction of the mixture and/or involves potentially dangerous infectious organisms.

The foremost example of an advantageous application of the above principles is in HIV (human immunodeficiency virus) infected patients, where there frequently exists a marked deficiency of the T4 population. We have modified the above protocol to successfully grow and enrich the T4 cells in vitro with the CD3,8 BSMAB. The major difference in the method is the addition of an anti-HIV agent such as azidothymidine (AZT) or soluble CD4 to the culture to prevent infection of the proliferated T4 cells. These T4 cells may then be further expanded by periodic stimulation with anti-CD3 MAB or PHA in the presence of irradiated feeder cells and the anti-HIV agents. Potentially these T4 cells can be reinfused to the patient in large quantity to combat infections and tumors. Ideally the patient should be concurrently treated with anti-HIV agents in vivo as well.

Alternatively, when no anti-HIV agents are added, the CD3, 8 BSMAB can be added in vitro to peripheral blood mononuclear cells or whole blood to rapidly induce HIV viral expression, which can then be assayed by commercial ELISA kit designed to detect HIV viral proteins. Our experiments indicated this method will detect viral expression at least as rapidly as the current cumbersome technique of coculturing the peripheral blood mononuclear with irradiated nonautologous feeder cells in the presence of PHA.

C. Selective Destruction and Proliferation of T Cell Subsets from Tissue

T cells infiltrating a diseased tissue may have beneficial effects (e.g. the tumorcidal properties of some tumor-infiltrating lymphocytes) or harmful effects, such as mediating the tissue destruction of rheumatoid synovium or graft. In either situation, direct growth and selection of the desired T cell subsets from the tissue (as opposed to selection from a heterogeneous population derived from tissue) will be useful both in therapeutic regimes and in the clinical study of immunotherapeutic potentials of either expanding the beneficial clones or of curtailing the harmful clones.

BSMABs may be used to selectively grow tissue-infiltrating T cell subsets directly from the tissue. For example, a small piece of tumor tissue from biopsy or surgery is minced into slices several millimeters thick and placed in IL2- and CD3,4- or CD3,8-containing media, at concentrations similar to that described for peripheral blood derived mononuclear cells. The antibody containing media is left in for 3–4 days and then partially exchanged. As the cell population expands, media is added to keep the concentration at 0.2–1.0 million cells/ml. When sufficient cells have grown, they may be stained and anti-tumor properties tested. Those exhibiting beneficial properties may be further propagated indefinitely with periodic mitogen stimulation in the presence of irradiated feeder cells as described above concerning culturing T cells. These T cell subsets may then be reinfused into the patients with IL2. In this way, the patient is infused with a population enriched with cells that have a beneficial effect, and detrimental cell populations are reduced.

D. Selective Immunoactivation of T-Cell Subset in Situ

For modulation of an undesired excessive immune response which occurs in graft rejection and autoimmune diseases, in vivo administration offers the advantages of rapid, direct blocking and targeting of the cells involved in the disease process. Our preliminary in vivo experiments in murine models suggested that the in vivo actions of BSMABs to a large extent parallel their actions in vitro with some differences. For example, injection of the antimurine CD8, IL2R BSMAB to mice spared the majority of the CD8+IL2R- population from tissues and peripheral circulation. At the same time no CD8+IL2R- population emerged from the treated mice that were immunized with the contact sensitizer trinitrobenzenesulfonic acid.

Injection of an anti-murine CD3, 4 BSMAB into normal mice at a dose range of 4–100ug/mouse produced a dose dependant, rapid preferential clearance (<4 hrs.) of CD4+ cells from the peripheral blood with a gradual reappearance of the CD4+ cells from days 2–7 stabilizing at reduced CD4+/CD8+ ratios. In the spleen, there was a more gradual reduction of the CD4+ cells over the first week in a dose dependent manner. The appearance of CD4-IL2R+ activated T cells appeared at one week for those mice treated with moderate to high doses of the antibody. Thus based on the murine model, one can examine a broad range of effects by titering the degree of CD4+ T cell reduction and alteration of the CD4+/CD8+ ratio in the both the peripheral blood and tissue with or without activation of the reciprocal T cell subset by altering the dose of BSMABs. This ability to partially modulate one T cell subset with activation of the reciprocal subset is potentially quite useful in activating tumor infiltrating lymphocytes (TIL) in the fight against tumor. By activating the TIL subset in situ in the tumor, one bypasses the homing problem of ex vivo propagated TIL (i.e. only a small minority of reinfused ex vivo propagated TIL managed to home back into the tumor). The preferential activation of one TIL subset with partial modulation of the reciprocal TIL subset would be particularly useful in the many tumors in which a TIL suppressor population can be demonstrated. In addition to a TIL effector population which is capable of lysing tumor cells, these tumors also contain a TIL suppressor subset capable of down regulating the antitumor response. This TIL suppressor subset may be of either the CD4+ or CD8+ phenotype depending on the particular tumor.

To test the various murine tumor models, a group of mice will be injected in the subxiphoid region with tumor cells at a concentration of $1-10 \times 10^4$ cells/mouse. The cells are allowed to grow for 10 days. The size of the tumor will be determined by two perpendicular measurements with a fine caliper every 3 days until death. An appropriate dosage of BSMAB or TSMAB is selected in the following manner: 52 C57BL/6 mice will be divided into 13 groups of 4 animals each. Group 1 will receive an injection of saline intravenously at day 0. Group 2–5 will receive 0.1 µg, 1.0 µg, 10 µg, and 100 µg of CD3, 4 intravenously per mouse respectively at day 0. Group 6–9 will receive 0.1 µg, 1.0 µg, 10 µg, and 100 µg of CD3, 8 intravenously per mouse on day 0. Group 10–13 will receive 0.5 µg, 5 µg, 50 µg, and 500 µg of 2C11 per mouse intravenously, the range established by Ellenhorn et al. (16). A small amount of blood will be collected in citrated tubes by nicking the tail vein from each group of animal (pooled for each group) on days, 0, 1, 3, 7, 10, and 30 stained for Thy 1, CD3, CD4, CD8, IL2R, TR, and DR expression for flow cytometry. On days 1, 3, 10, and 30 one animal from each group will be sacrificed. The spleen, thymus, and inguinal lymph nodes will be removed and two thirds of the tissue will be extracted, part stained for flow cytometry, part used for determining cytolytic capacity against the NK-sensitive YAC-1 lymphoma (ATCC) and LAK-sensitive MCA-102 sarcoma, and part used for determining secretion of IL2 and TNF-α without further in vitro stimulation. Supernatant from different time point collected for cytokine production will be quickly frozen and thawed together. IL2 will be measured by the supernatant's effect on the IL2-dependent CTLL (ATCC) growth. TNA-α will be measured by western-blot kit produced by Genzyme, Boston, Mass. The other third of the tissue will be prepared for immunohistochemical staining for the same markers in situ. Long tern trend determined from this experiment will then confirmed in a separate experiment where the mice will be monitored monthly without being sacrificed. Dividing the higher doses into different days will also be examined. Serum from day 10 and 30 will also be checked for the presence of anti-idiotypic antibodies by their ability to block fluorochrome-conjugated 2C11, 2.43 (anti-Lyt2), and GK1.5 (anti-L3T4) and mouse-anti-rat and anti-hamster Ig antibodies detected by ELISA and mouse Ig-specific antiserum. The subject mice are then injected daily (i.v.) with the appropriate amount of BSMAB or TSMAB. Animals will sacrificed on days 1, 3, 7, and 14 after antibody treatment and the tumor sectioned for immunohistochemical staining and assayed for TIL-mediated cytotoxicity and lymphokine production. In animals whose tumors show partial response to treatment, a repeat injection of the same antibody at either the same or slightly higher dose will be administered. Repeat injection will continue to be administered every 7–10 days as long as the tumor shrinks or delays its growth. Efficacy will be determined, as above. Cytokines such as IL2, α-IFN, and $_{65}$-IFN may be administered concurrently, in doses sufficiently low to avoid toxicity. Such doses may be translated from animal studies optimizing dosage.

CD4 and CD8 Epitopes

We have found that the epitope to which OKT4 binds is not optimal for many reasons. Accordingly, we prefer to use anti-CD4 antibodies that effectively do not compete with OKT4, i.e., that bind to a different epitope from the epitope recognized by OKT4.

The CD4 and CD8 molecules each have several epitopes to which antibody can bind. The effect of anti-CD4 or anti-CD8 MABs therefore may differ considerably depending on the particular epitope that they bind. In particular, OKT4 is not optimal in various aspects of the invention. For this reason, we have also developed a series of anti-CD4 MAB's termed the JET4 series. JET4A partially overlaps the OKT4 epitope, but not the Leu 3a epitope. It blocks HIV infection well. JET4B does not block either the OKT4 or Leu-3a epitope. It stains tissue very strongly. 3G3 similarly is an anti-CD8 antibody that does not crossblock OKT8 or Leu-2a. We have synthesized new CD3,4 and CD3,8 BSMABs using these antibodies.

Selective Targeting of Cells That Coexpress Two Different Surface Antigens

We have further demonstrated that appropriate BSMABs can promote complement-mediated lysis of target cells (ADCMC) that bear both surface antigens far more efficiently than those that express only one of the antigens. This selectivity of appropriate BSMABs also applies for ADCC, another major antibody-dependent effector mechanism of the immune system. This selectivity also generally enhances the effect of BSMABs having a toxin/drug to the Fc portion of the molecule. The enhancement contrasts prior disclosures where the BSMAB is bound to the toxin/drug via one antigen binding site, allowing only one antigen binding site to be free to bind to the target cell. Such earlier techniques therefore cannot be used to selectively target cells that coexpress two different surface antigens. We have also demonstrated that appropriate BSMABs can selectively stain cells in tissue or fluids that coexpress two different surface antigens.

Examples of the useful selectivity of BSMABs include the selective targeting of activated T cell subsets, of a particular subcategory of T cell subsets, and of tumors. T cells have to be activated to carry out many of their functions, and T cells involved in pathogenesis of diseases, such as autoimmune diseases and graft rejection, presumptively are in the activated fraction during a flareup of the disease. By selectively targeting the activated T cell or T cell subsets for immunotherapy, one may then attack the incriminated cells but leave most of the noninvolved T cells of that subset intact to carry out their normal immune functions in the future. Known activation markers, including the IL2 receptor, are not unique to any T cell subsets or even to T cells.

Although not T cell subset specific, CD3, IL2R BSMABs in this case combine the advantages of both the anti-CD3 antibodies which are highly potent but, as described above, inherently lack specificity, and the higher specificity but low potency of anti-activation marker antibodies such as anti-IL2R. This combination would be particularly useful in situations where both T cell subsets may be involved.

It may be desirable to leave intact the activated suppressor cells in graft rejection or autoimmune diseases while attacking the activated T helper cells. Thus the above-described anti-IL2/anti-T subset BSMABs offer distinct advantages over conventional anti-IL2 MABs.

As outlined in the selective destruction and proliferation section, in some situations, one may wish to selectively target the inducer of B cell help or inducer of suppressor cells. The former may be characterized by a combination of CD4 and CDw29 and the latter by a combination of CD4 and CD45R. Neither is characterizable by any of the antigens by themselves. Similarly the cytotoxic T8 cells may be characterized by a combination of CD8 and CD28 but not by either antigen alone. This invention offers an alternative means of selectively targeting specific subcategories of the major T cell subsets.

Most tumor antigens are not unique to the tumor but are also expressed by certain normal tissues in a characteristic pattern. By choosing a BSMAB that recognizes two tumor associated antigens with nonidentical tissue distribution, one can limit the degree of normal tissue involved while the tumor is attacked.

The selective staining capability of BSMAB for cells that coexpress two different surface antigens can be used to double the specificity of monoclonal antibodies in diagnosis and in the study of the cellular involvement in a disease process.

In vitro selective elimination of cells that coexpress the two antigens may be accomplished by incubating the cells at concentration of 2–10 million/ml in the presence of the appropriate BSMAB. The optimal concentration for selectivity varies for each BSMAB. It was about 0.5–1.0 ug/ml for CD3,4 and about 0.01–0.1 ug/ml for CD3,8. This may be incubated for 30–60 min. at room temperature followed by addition of a 1 to 2–4 dilution of young rabbit serum (Pel-Freez Biological, Rogers, Ariz.), incubated at room temperature for another 60 min., and then washed away the antibody and complement.

The antibody concentration range providing optimum selectivity for antibody dependent complement-mediated cytotoxicity can be determined by the method of Wong and Colvin, *J. Immunol.* 139:1369–1374 (1987); or by the NIH protocol; Teresaki et al., Am. *J. Clin. Path.* 69:103 (1978). One microliter ($3.5 \times 10^3$ cells) was added to each well of a Terasaki plate (precoated with mineral oil). Five microliters of the test solution were then added and allowed to incubate at RT for 40 to 45 min. Five microliters of a ½ dilution of 3- to 4-wk-old rabbit serum (Pel-Freez Biological, Rogers, Ariz.) were next added at RT for 60 min. Five microliters of 4% eosin were added for 3 min. followed by 5 µl of 2% paraformaldehyde. The plates were then viewed with a phase contrast microscope.

The concentration range for destroying target cells coexpressing the two antigens, without significant destruction of cells expressing only one of the antigens, can be determined as described above.

Similarly, the optimum concentration range for ADCC can be determined by the technique of Kipps et al., *J. Exp. Med.* 161:1–17 (1985), except that the target cells will be those that express both antigens recognized by the bispecific monoclonal antibody. Antibody will be added in increasing concentrations. Effector cells used are the U937 cell line treated with 1000U/ml of $\gamma$-interferon or adherent cells from peripheral blood.

At present we have developed the JET4b,OKT9; OKT8, OKT9; 3G3,7E11(anti-IL2 receptor); other combinations, e.g., JET4b,7E11; 12F6,7E11 can readily be made.

Selective Inhibition of Cytolytic T Cell Subsets

Triggering of the Ti/CD3 receptor complex is important in T cell-mediated killing of target cells, as evidenced by the ability of anti-CD3 or anti-Ti MABs to block cytolytic activity. See, Leontsini et al., *J. Cell Immunol.* 102:21 (1986); and Shaw et al., *J. Immunol.* 134:3019 (1985). CD4 and CD8 are believed to aid in this function by increasing the adhesion between the effector and target cells. See, Moretta et al., *J. Exp. Med.* 159:P921 (1984). Both anti-CD3 and anti-CD8 MABs have been demonstrated to be effective in aborting graft rejection in vivo.

The in vitro blocking effect of the anti-CD3 MAB, anti-CD8 MAB, and CD3,8 BSMAB on a T8 cytolytic clone against its target was studied using a chromium release assay. CD3,8 BSMAB was more effective than either the parental anti-CD3 or anti-CD8 MABs at a much lower concentration when continuously left in cultures. In contrast, CD3, 8 BSMAB had little blocking effect of a T4 cytolytic clone against its target. Similarly CD3, 4 BSMAB was more effective than the parent anti-CD3 and anti-CD4 antibodies in blocking the T4 cytolytic clone but not in blocking the T8 cytolytic clone. The increased potency is likely secondary to concurrent crossblocking of two structures critical to the cytolytic or activation process. This preferential blocking will enhance the other selective immunotargeting processes described earlier.

Effectuation of Selective Immunotargeting with BSMABs

Effectuation of selective cell destruction will take advantage of the patient's own immune system, such as the ADCC, and the ADCMC, the latter relying on complement recruited by the BSMAB for lysis of the target cells. Murine IgG2a (for Fc of the BSMAB) has the advantage of higher ADCC potential. Murine IgG3 has the advantage of fixing human complement well. Human Fc may be used also.

Toxin-conjugated BSMABs may also be used to increase potency.

Selective delivery of drugs or toxins to cells that coexpress two different surface antigens may be accomplished by conventional protocols. See, e.g. U.S. Pat. No. 4,542,225 and references cited therein.

Selective staining of cells that coexpress two different surface antigens may be done according to conventional immunoperoxidase or fluorochrome methods. The slide mounted tissue is first incubated with the BSMAB for 1–12 hrs, washed several times, then biotin conjugated goat-anti-mouse antibodies are added and incubated for another 1–2 hours. This is again washed 3 times and then avidin conjugated horse radish peroxidase is added, incubated for several hours, and washed. Then enzyme substrate is added and developed before washing and fixing. A particular useful combination for tissue staining is CD3,4 BSMAB where the CD4 binding portion has good tissue staining ability—i.e., it does not bind to the OKT4 epitope. Such BSMAB's help to distinguish CD3+CD4+ T cells from CD4+ monocytes and macrophages.

Synthesis and Use of TSMABs

Figure 1:
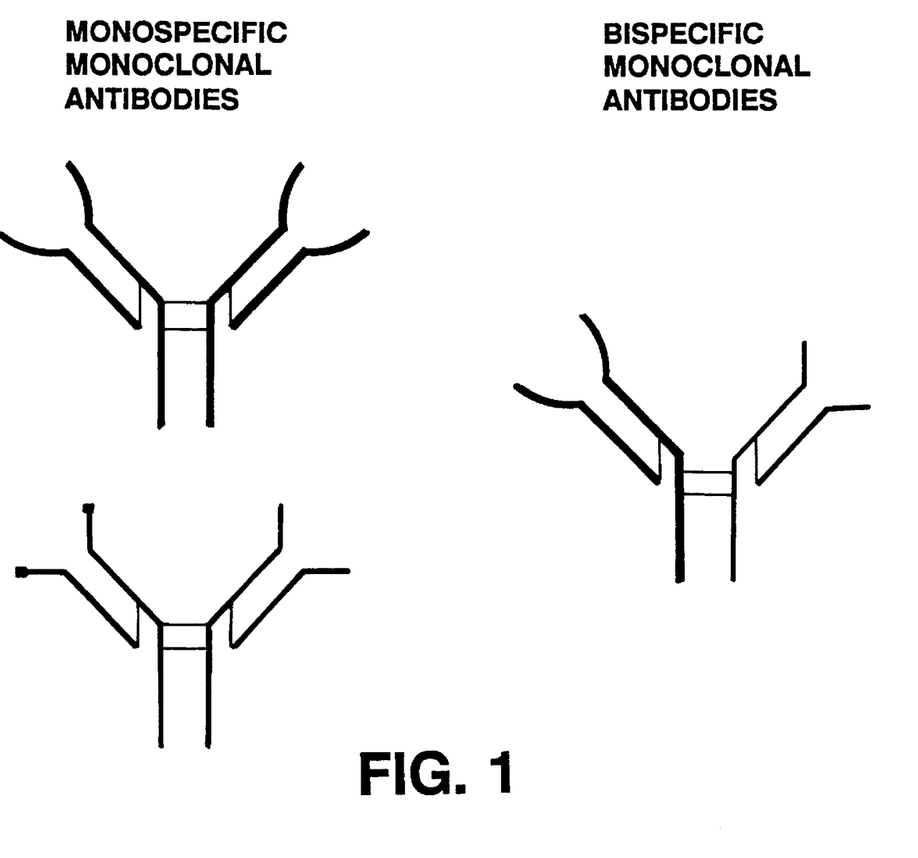
FIG. 1 is a highly schematic diagram of a BSMAB, showing the origin of its Fc portion and its two FAB portions from two different MAB's.
Figure 2:
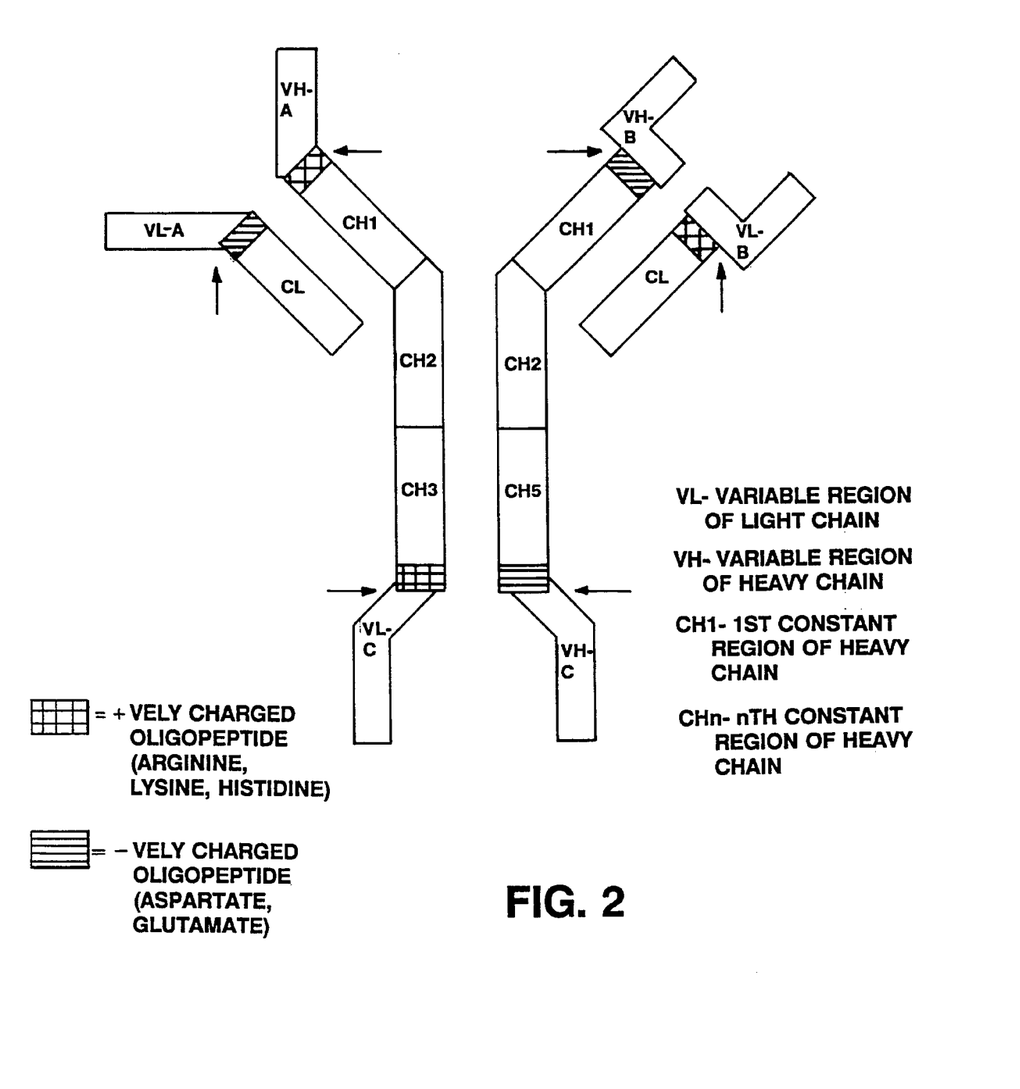
FIG. 2 is a schematic diagram of a TSMAB, showing an intact Fc portion, variable regions A, B, and C, and regions of complementary positive and negative charge.
Figure 3:
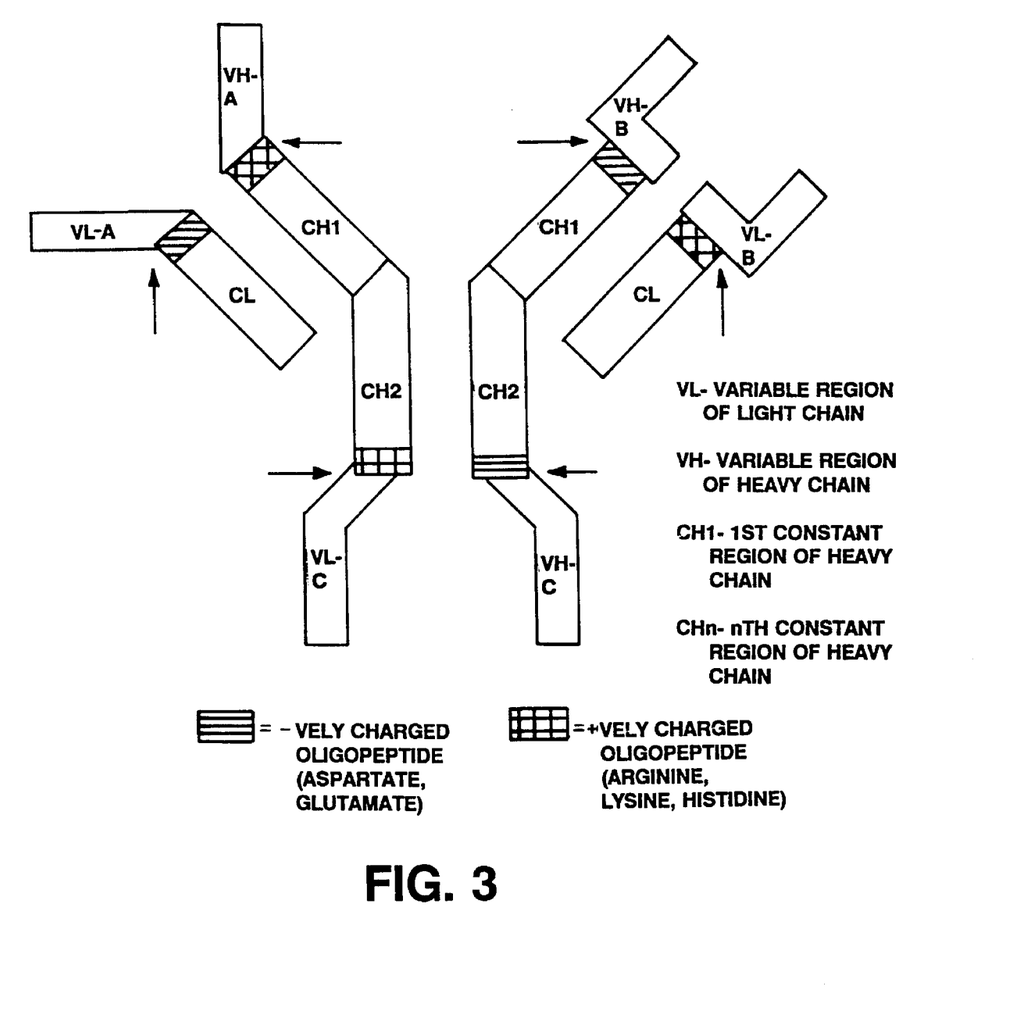
FIG. 3 is a schematic diagram of a TSMAB, as in FIG. 2, but with portion of the Fc region deleted.
Figure 4:
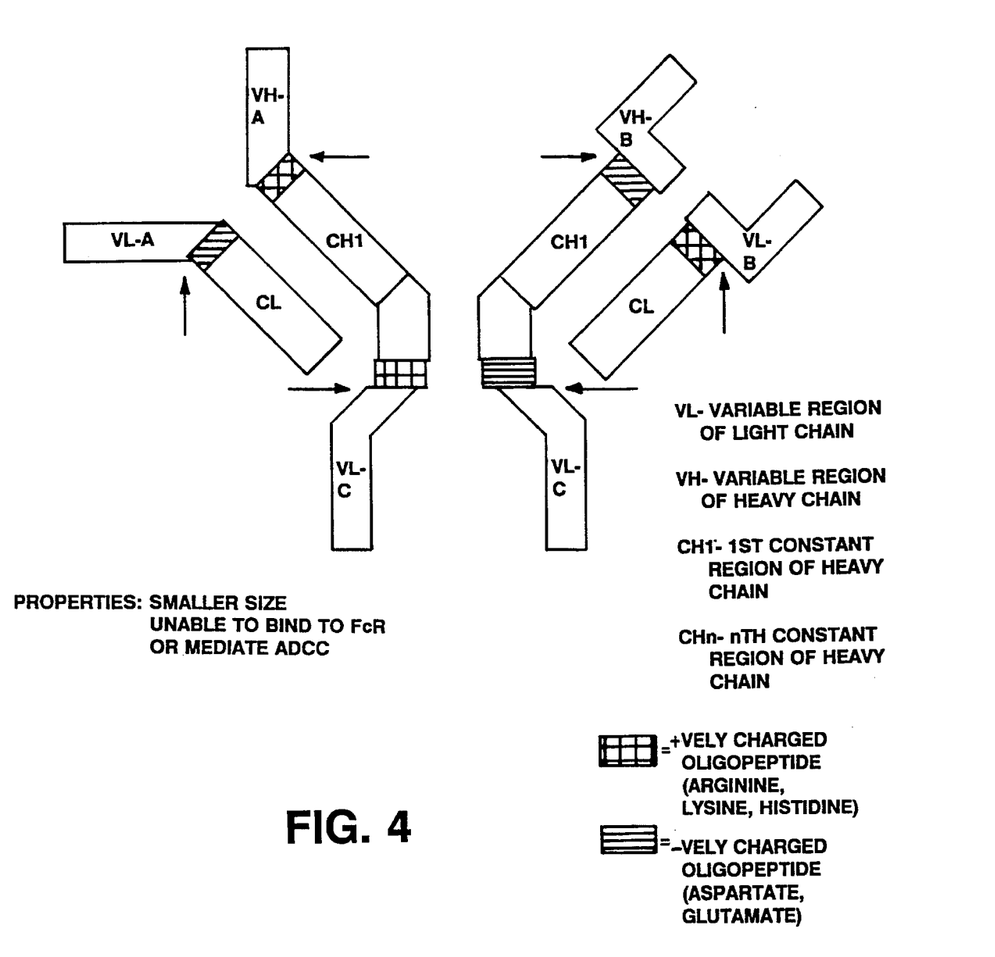
FIG. 4 is a schematic diagram of a TSMAB, as in FIG. 2, but with the entire Fc region deleted.

TSMABs incorporate a third binding site (c) in the Fc portion of the antibody. TSMABs can be genetically engineered using well established recombinant molecular biology techniques of splicing different gene segments using restriction endonucleases. A separate splicing will be needed at each of the indicated sections, though many partially spliced fragments can serve as useful templates for many different combinations. It will be useful to splice in small regions of charged amino acid groups such that the heavy chains will preferentially combine with the partner chain and repel identical chains. Similarly, such complementary charged regions will allow preferential combinations of the desired heavy and light chains. The gene combinations can then be sequentially transfected into the appropriate myeloma cell lines using standard techniques. In particular, the Fc binding region may be anti-CD3 or anti-Ti. This TSMAB would further promote lysis of specific T-cell subpopulations by providing an additional region for binding the cytolytic T lymphocytes (CTL). Alternatively, the Fc region may bind a drug or toxin, or a stain, as discussed in VI, above. These TSMABs would have the additional advantage of providing a two-step identification or destruction process, in that the stain, drug or toxin could be administered after the initial binding of the TSMAB at the target site selected by binding in regions A and B.

Other Embodiments

Other embodiments are within the following claims.

We claim:

1. A bispecific monoclonal antibody having a common Fc portion, a first FAB portion specific for CD3 and a second FAB portion specific for the interleukin-2 receptor, CD28, CD45 or CDTfr.

2. A method of detecting HIV viral proteins in peripheral blood mononuclear cells or whole blood wherein a bispecific CD3/CD8 monoclonal antibody is first added in vitro to said peripheral blood mononuclear cells or said whole blood rapidly induce HIV viral expression.

3. A bispecific monoclonal antibody having a common Fc portion, a first FAB portion specific for CD3 and a second FAB portion specific for the interleukin-2 receptor.

4. A bispecific monoclonal antibody having a common Fc portion, a first FAB portion specific for CD4 and a second FAB portion specific for the interleukin-2 receptor.

5. A bispecific monoclonal antibody having a common Fc portion, a first FAB portion specific for CD8 and a second FAB portion specific for the interleukin-2 receptor.

6. An in vitro method of decreasing the ration of mammalian TX cells/mammalian TY cells in a mixture of cells, where said TX cells and said TY cells each bear CD3 antigen and said TX cells also bear a second mammalian T cell surface antigen, CD4, not present on said TY cells, said method comprising contacting said mixture with a CD3/CD4 bispecific antibody.

7. An in vivo method of decreasing the ratio of TX cells/TY cells in a mammal, where said TX cells and said TY cells each bear CD3 antigen and said TX cells also bear a second mammalian T cell surface antigen, CD4, not present on said TY cells, said method comprising administering to said mammal a CD3/CD4 bispecific antibody.

8. The method of claim 6 further comprising culturing said cells under proliferating conditions after contacting them with said CD3/CD4bispecific antibody.

9. A method for selectively proliferating CD8 T-cells in a patient comprising administering to said patient a CD3/CD4 bispecific monoclonal antibody.

10. A method for selectively depleting CD4 T-cells in a patient comprising administering to said patient a CD3/CD4 bispecific monoclonal antibody.

11. An in vitro method for selectively proliferating CD8 T-cells in a mixture of cells containing T-cells, said method comprising incubating said mixture of cells with a CD3/CD4 bispecific monoclonal antibody.

12. An in vitro method for selectively depleting CD4 T-cells in a mixture of cells containing T-cells, said method comprising incubating said mixture of cells with a CD3/CD4 bispecific monoclonal antibody.

13. The method of claim 6 or 7 wherein the FAB portion of said CD3/CD4 bispecific antibody is substantially non-competitive with OKT4.

14. An in vitro method of decreasing the ratio of mammalian TX cells/mammalian TY cells in a mixture of cells, where said TX cells and said TY cells each bear CD3 antigen and said TX cells also bear a second mammalian T cell surface antigen, CD8, not present on said TY cells, said method comprising contacting said mixture with a CD3/CD8 bispecific antibody.

15. An in vivo method of decreasing the ratio of TX cells/TY cells in a mammal, where said TX cells and said TY cells each bear CD3 antigen and said TX cells also bear a second mammalian T cell surface antigen, CD8, not present on said TY cells, said method comprising administering to said mammal a CD3/CD8 bispecific antibody.

16. The method of claim 14 further comprising culturing said cells under proliferating conditions after contacting them with said CD3/CD8 bispecific antibody.

17. A method for selectively proliferating CD4 T-cells in a patient comprising administering to said patient a CD3/CD8 bispecific monoclonal antibody.

18. A method for selectively depleting CD8 T-cells in a patient comprising administering to said patient a CD3/CD8 bispecific monoclonal antibody.

19. An in vitro method for selectively proliferating CD4-bearing T-cells in a mixture of cells containing T-cells, said method comprising incubating said mixture of cells with a CD3/CD8 bispecific monoclonal antibody.

20. An in vitro method for selectively depleting CD8 T-cells in a mixture of cells containing T-cells, said method comprising incubating said biological sample with a CD3/CD8 bispecific monoclonal antibody.

21. The method of claim 19 or 20 wherein said mixture of Cells is obtained from a patient infected with HIV.

22. The method of claim 17 or 18 wherein said patient is infected with HIV.

23. The method of claim 17 or 18 wherein said patient is being treated with an anti-viral drug.

24. A method for selectively targeting T-cells bearing both antigens recognized by a bispecific monoclonal antibody comprising contacting a mixture of cells containing T-cells with a bispecific monoclonal antibody selecting from the group consisting of: CD3/CD8; CD3/CD4; CD3/CD28; CD4/interleukin-2 receptor; CD8/interleukin-2 receptor; and CD8/CDTfr.

25. The method of claim 16 wherein said bispecific monoclonal antibody is linked to a drug.

26. The method of claim 16 wherein said bispecific monoclonal antibody is linked to a detectable label.

27. The method of claim 24 wherein said contacting occurs in vitro.

28. An in vitro method for detecting HIV in a population of cells comprising T cells, said method comprising first incubating said population of cells in vitro with CD3/CD8 and then measuring the level of an HIV protein.

29. A bispecific monoclonal antibody having a common Fc portion, a first FAB portion specific for CD8 and a second FAB portion specific for Transferrin receptor.

30. A bispecific monoclonal antibody having a common Fc portion, a first FAB portion specific for CD4 and a second FAB portion specific for Transferrin receptor.

31. A bispecific monoclonal antibody having a common Fc portion, a first FAB portion specific for CD3 and a second FAB portion specific for the interleukin-2 receptor.

32. The method of claim 24 in which said bispecific monoclonal antibody is linked to a detectable label, whereby cells bearing both said antigens recognized by said bispecific monoclonal antibody are selectively labeled.

33. The method of claim 24 in which said bispecific monoclonal antibody is linked to a drug whereby cells bearing both said antigens recognized by said bispecific monoclonal antibody selectively receive said drug.

34. The method of claim 24 further comprising exposing said mixture to an ADCC or an ADCMC effector system.

* * * * *